United States Patent
Hébert et al.

(10) Patent No.: US 10,466,105 B2
(45) Date of Patent: Nov. 5, 2019

(54) REMOTE SPECTROSCOPY DEVICE WITH A COMPOSITE LASER SOURCE AND ASSOCIATED REMOTE SPECTROSCOPY METHOD

(71) Applicants: CENTRE NATIONAL D'ETUDES SPATIALES, Paris (FR); Office National d'Etudes et de Recherches Aérospatiales, Palaiseau (FR)

(72) Inventors: Philippe Hébert, Toulouse (FR); François Lemaître, St Orens de Gameville (FR); Xavier Orlik, Pechabou (FR); Thibault Dartigalongue, Toulouse (FR)

(73) Assignees: CENTRE NATIONAL D'ETUDES SPATIALES, Paris (FR); Office National d'Etudes et de Recherches Aérospatiales, Palaiseau (FR)

( * ) Notice: Subject to any disclaimer, the term of this patent is extended or adjusted under 35 U.S.C. 154(b) by 0 days.

(21) Appl. No.: 15/986,445

(22) Filed: May 22, 2018

(65) Prior Publication Data
US 2018/0340829 A1 Nov. 29, 2018

(30) Foreign Application Priority Data
May 23, 2017 (FR) ...................... 17 54568

(51) Int. Cl.
*G01J 3/427* (2006.01)
*G01N 21/31* (2006.01)

(52) U.S. Cl.
CPC .......... *G01J 3/427* (2013.01); *G01N 21/3151* (2013.01); *G01N 2201/06113* (2013.01)

(58) Field of Classification Search
None
See application file for complete search history.

(56) References Cited

U.S. PATENT DOCUMENTS

| | | | | |
|---|---|---|---|---|
| 7,969,576 | B1 * | 6/2011 | Buckley | G01N 21/39 356/437 |
| 9,086,374 | B1 * | 7/2015 | Demers | G01N 21/3563 |
| 2011/0080580 | A1 * | 4/2011 | Fermann | G01N 21/31 356/301 |
| 2015/0159990 | A1 * | 6/2015 | Plusquellic | G01N 21/255 356/451 |
| 2016/0109294 | A1 * | 4/2016 | Kasper | G01J 3/4338 250/339.07 |

(Continued)

FOREIGN PATENT DOCUMENTS

FR     3039331 A1   1/2017

*Primary Examiner* — Shawn Decenzo
(74) *Attorney, Agent, or Firm* — Burris Law, PLLC

(57) ABSTRACT

Disclosed is a remote spectroscopy device of the LIDAR type including a module for generating an emission signal, an emission module for sending the emission signal toward a targeted material, a receiving module for receiving a response signal and a module for postprocessing of the response signal to determine a composition of the targeted material. The generating module includes at least two laser sources, each laser source being able to generate a laser signal at a predetermined wavelength, an upstream mixer able to mix the laser signals generated by the different laser sources, and a first modulator able to modulate the composite signal at a first modulation frequency to form the emission signal.

9 Claims, 2 Drawing Sheets

(56) References Cited

U.S. PATENT DOCUMENTS

| | | | |
|---|---|---|---|
| 2017/0227461 A1* | 8/2017 | Chen | G01N 21/55 |
| 2017/0292875 A1* | 10/2017 | Song | G01N 21/3581 |
| 2018/0073976 A1* | 3/2018 | Imoto | G01N 21/01 |
| 2018/0271363 A1* | 9/2018 | Scheibler | A61B 3/10 |

\* cited by examiner

REMOTE SPECTROSCOPY DEVICE WITH A COMPOSITE LASER SOURCE AND ASSOCIATED REMOTE SPECTROSCOPY METHOD

FIELD OF THE INVENTION

The present invention relates to a remote spectroscopy device with a composite laser source.

The present invention further relates to a remote spectroscopy method implemented by this device.

BACKGROUND OF THE INVENTION

Various remote spectroscopy methods are already known in the state of the art. One example of such a spectroscopy method is in particular described in application FR 3,039,331.

This spectroscopy method is said to be of the "LIDAR" type, which means that it is carried out by an optical remote detection and measuring tool known under the term "LIDAR". The term "LIDAR" comes from the expression "light detection and ranging".

In particular, this method makes it possible to study the composition of a targeted material located at a distance from the LIDAR by emitting a light wave toward this material with a determined frequency, and then receiving a light wave reflected by this material.

Thus, by comparing this reflected light wave with the initial wave or with a reference signal, it is for example possible to determine the absorption coefficient by the material, which generally makes it possible to determine the precise composition of this material.

The light wave is emitted by the LIDAR in the form of a frequency comb generally made up of a plurality of light rays. These rays are generated from a laser signal by one or several modulators with a predetermined frequency, using generating methods known in themselves. This frequency is in particular chosen based on the desired sampling fineness.

All of the rays of the comb are sent simultaneously toward the targeted material, subsequently reflected by this material and received by the LIDAR. By mixing with the reference signal, the received light ray makes it possible to obtain an interferogram of the targeted material. Its Fourier transform then provides a spectrum of the targeted material, i.e., a precise composition of this material.

Each emitted light ray then makes it possible to cover a predetermined wavelength domain by the LIDAR.

However, for certain targeted materials, the wavelength domain of the existing spectroscopy devices is relatively restricted, which does not make it possible to study these materials sufficiently.

SUMMARY OF THE INVENTION

The present invention aims to considerably broaden the wavelength domain reachable by remote spectroscopy in order to be able to analyze all of the targeted materials more effectively.

To that end, the invention relates to a remote spectroscopy device of the LIDAR type including a generating module for generating an emission signal; an emission module for sending the emission signal toward a targeted material; a receiving module for receiving a response signal corresponding to the emission signal reflected by the targeted material; a module for postprocessing of the response signal to determine a composition of the targeted material.

The generating module includes at least two laser sources, each laser source being able to generate a laser signal at a predetermined wavelength different from the wavelength of the or each other laser source; an upstream mixer able to mix the laser signals generated by the different laser sources to form a composite signal; and a first modulator able to modulate the composite signal to a first modulation frequency to form the emission signal.

According to other advantageous aspects of the invention, the device comprises one or more of the following features, considered alone or according to all technically possible combinations:

- the postprocessing module includes a main filter able to extract, from the received response signal, elementary signals corresponding to the different predetermined wavelengths;
- the generating module further includes a separator of the composite signal or the emission signal to form a reference signal intended for the postprocessing module;
- the postprocessing module further includes a complementary filter able to extract, from the reference signal, elementary signals corresponding to the different predetermined wavelengths;
- the generating module further includes a second modulator able to modulate the composite signal at a second modulation frequency different from the first modulation frequency;
- the generating module further includes a downstream mixer able to mix the composite signal modulated by the first modulator and the composite signal modulated by the second modulator to form the emission signal;
- the first modulation frequency is chosen based on physical characteristics of the targeted material; and
- the predetermined wavelengths are chosen based on physical characteristics of the targeted material.

The invention also relates to a remote spectroscopy method including the following steps:
- generating an emission signal;
- sending the emission signal toward a targeted material;
- receiving a response signal corresponding to the emission signal reflected by the targeted material;
- analyzing the response signal to determine a composition of the targeted material.

The step for generating the emission signal comprises the following sub-steps:
- generating at least two laser signals at different predetermined wavelengths;
- mixing the generated laser signals to form a complex signal; and
- modulating the composite signal at a first modulation frequency to form the emission signal.

According to other advantageous aspects of the invention, the method comprises one or more of the following features, considered alone or according to all technically possible combinations:

- the step for generating the emission signal further comprises the following sub-steps:
  - modulating the composite signal at a second modulation frequency to form the emission signal;
  - mixing the composite signals modulated at the first and second modulation frequencies to form the emission signal;
- the step for analyzing the response signal comprises the following sub-step:

extracting, from the received response signal, elementary signals corresponding to the different predetermined wavelengths;

the step for generating the emission signal further comprises the following sub-step:

separating the emission signal to form a reference signal;

the step for analyzing the response signal further comprises the following sub-step:

extracting, from the reference signal, elementary signals corresponding to the different predetermined wavelengths.

BRIEF DESCRIPTION OF THE DRAWINGS

These features and advantages of the invention will appear upon reading the following description, provided solely as a non-limiting example, and done in reference to the appended drawings, in which.

DETAILED DESCRIPTION OF THE INVENTION

Figure 1:
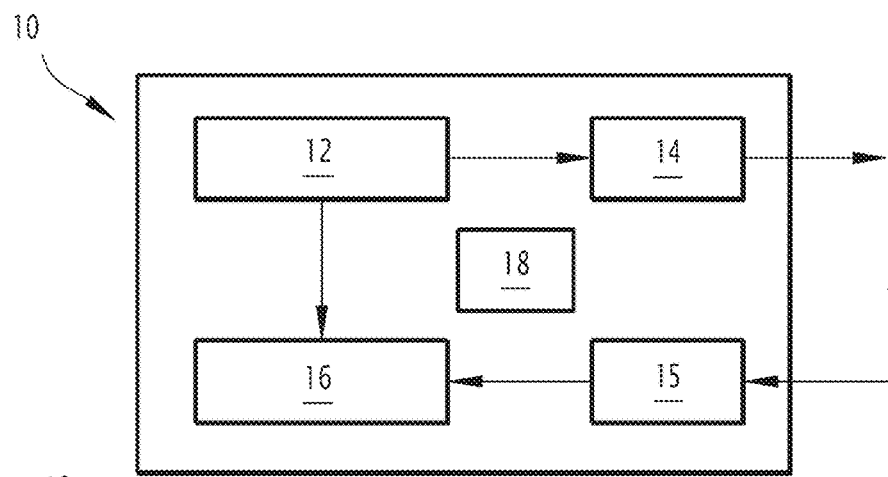
FIG. 1 is a schematic view of a remote spectroscopy device according to the invention, the remote spectroscopy device in particular including a generating module and a post-processing module.

The spectroscopy device 10 of FIG. 1 is for example on board a satellite on a terrestrial orbit and making observations of the Earth, or another planet, and in particular an atmospheric layer with a thickness for example equal to 15 km.

The spectroscopy device 10 makes it possible to study a targeted material in this atmospheric layer. The targeted material is for example a gas made up of several elementary gases, for example $CO_2$, $H_2O$ or $CH_4$.

Each elementary gas is able to absorb a light wave at a determined frequency with an absorption coefficient that is known a priori.

Thus, the spectroscopy device 10 for example makes it possible to determine the densities of the elementary gases contained in the targeted gas by sending a light signal toward the targeted gas and analyzing a signal reflected by this gas, or absorbed by it and reflected by a background surface.

According to one alternative embodiment, the spectroscopy device 10 is on board another spatial or land vehicle, or an aircraft.

According to still another alternative embodiment, the spectroscopy device 10 is arranged in a fixed manner, for example on the earth's surface.

In at least some of the aforementioned alternative embodiments, the spectroscopy device 10 further makes it possible to study a targeted material arranged in any medium other than the atmosphere, for example the underwater or underground medium.

In reference to FIG. 1, the spectroscopy device 10 includes a generating module 12, an emission module 14, a reception module 15, a postprocessing module 16 and a control module 18.

The generating module 12 is able to form an emission signal and a reference signal that are respectively intended for the emission module 14 and the postprocessing module 16.

The emission module 14 is an emission telescope known in itself that is able to receive the emission signals from the generating module 12 and send them toward the targeted material.

The receiving module 15 is a receiving telescope also known in itself that is able to receive response signals corresponding to the emission signals emitted by the emission module 14 and reflected by the targeted material or another material.

According to one alternative embodiment, the telescopes of the emission 14 and receiving 15 modules assume the form of a single component.

The postprocessing module 16 is able to receive the initial reference signals generated by the generating module 12 and the response signals received by the receiving module 15 and to analyze these signals to determine the precise composition of the targeted material.

The control module 18 makes it possible to control the operation of all of the modules of the spectroscopy device 10.

The control module 18 is for example connected to a central computer (not shown) of the satellite, from which it is commanded.

The generating module 12 and the postprocessing module 16 will now be explained in more detail in reference to FIG. 2.

Figure 2:
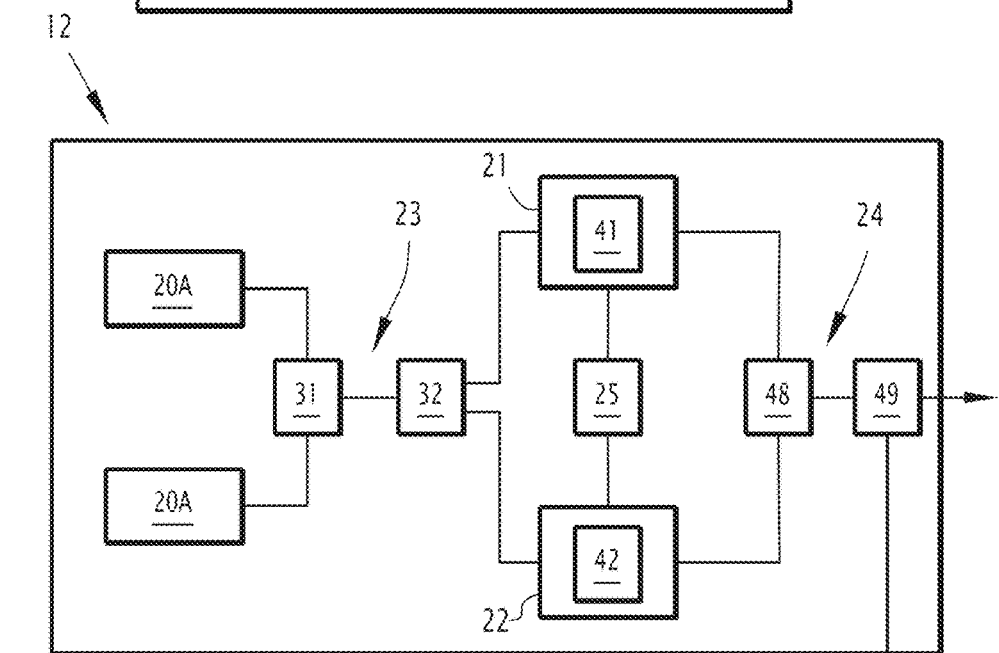
FIG. 2 is a schematic view of the generating module and the post-processing module FIG. 1.
Figure 2:
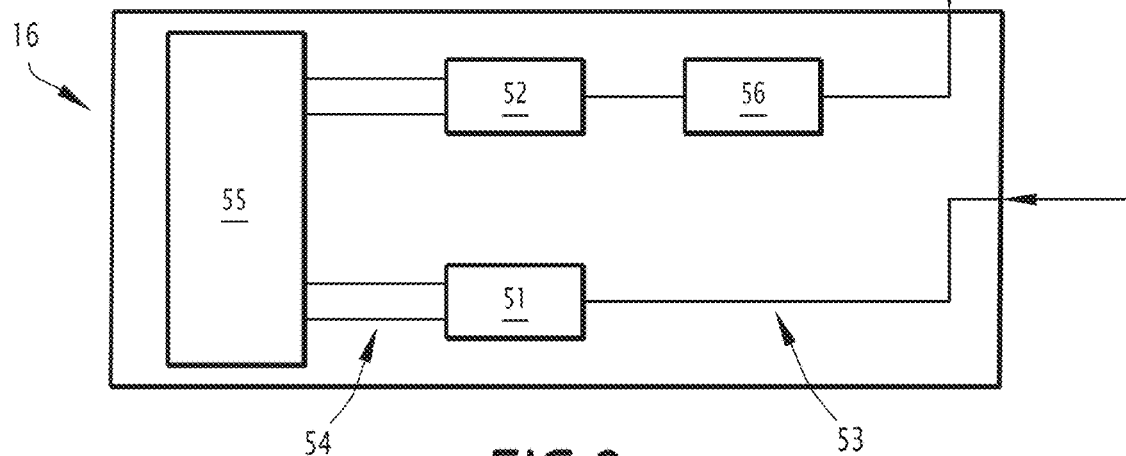

Thus, as illustrated in this FIG. 2, the generating module 12 includes two laser sources 20A, 20B, two optical channels 21, 22 connected to the laser sources 20A, 20B by upstream guide means 23 and two the emission 14 and postprocessing 16 modules by downstream guide means 24, and an electronic device 25 for managing optical channels 21, 22.

Each laser source 20A, 20B is able to generate a laser signal at a predetermined wavelength, respectively designated by $\lambda_A$ and $\lambda_B$. The wavelength $\lambda_A$ is different from the wavelength $\lambda_B$. These predetermined wavelengths $\lambda_A$, $\lambda_B$ are for example chosen based on physical characteristics of the targeted material. The upstream guide means 23 comprise an upstream mixer 31 and an upstream separator 32 successively connected by guide means, between the laser sources 20A, 20B on one side and the optical channels 21, 22 on the other.

In particular, the upstream mixer 31 is able to mix the laser signals generated by the different laser sources 20A, 20B to form a composite signal at its outlet.

The upstream separator 32 is able to divide each composite signal formed by the upstream mixer 31 into two equal portions intended for the two optical channels 21, 22. Hereinafter, each of these portions will be referred to interchangeably as "composite signal".

The optical channel 21, hereinafter called first optical channel, includes a first modulator 41 able to modulate the composite signal passing through this channel 21 to form a first modulated signal.

The first modulator 41 is for example an electro-optical modulator known in itself making it possible to generate a frequency comb I modulating the composite signal corresponding to a first modulation frequency $F_1$ for example equal to 1 GHz. This frequency comb is then comprised in the first modulated signal.

The optical channel 22, hereinafter called second optical channel, includes a second modulator 42 able to modulate the composite signal passing through this channel 22 to form a second modulated signal.

Like for the first modulator 41, the second modulator 42 is for example an electro-optical modulator known in itself making it possible to generate a frequency comb I modulating the composite signal corresponding to a second modulation frequency $F_2$ for example equal to $F_1+100$ KHz. This frequency comb is then comprised in the second modulated signal.

The electronic management device 25 makes it possible to control the operation of the modulators 41 and 42 according to techniques known in themselves. More particularly, the electronic device 25 is able to generate a radiofrequency signal with frequency $F_1$ controlling the operation of the first modulator 41 and a radiofrequency signal with frequency $F_2$ controlling the operation of the second modulator 42.

The downstream guide means 24 include a downstream mixer 48 and a downstream separator 49 connected by waveguides, successively between the optical channels 21, 22 on one side and the emission 14 and postprocessing 16 modules on the other.

In particular, the downstream mixer 48 makes it possible to form a signal made up of the first modulated signal coming from the first optical channel 21 and the second modulated signal coming from the second optical channel 22. The downstream mixer 48 thus causes the combs generated by these different channels to beat together and then generates an interferogram.

The downstream separator 49 makes it possible to separate the composite signal coming from the downstream mixer 48 into a weak part and a strong part, for example in a 10%:90% proportion. The weak part forms the reference signal intended for the postprocessing module 16 and the strong part forms the emission signal intended for the emission module 14. Each of the reference signal and the emission signal then comprises an interferogram.

The postprocessing module 16 comprises a main filter 51, an additional filter 52, upstream guide means 53, downstream guide means 54 and a processing unit 55.

The upstream guide means 53 have waveguides connecting the main 51 and additional 52 filters respectively to the receiving 15 and generating 12 modules.

In particular, the upstream guide means 53 make it possible to send each response signal coming from the receiving module 15 to the main filter 51 and each reference signal coming from the generating module 12 to the additional filter 52.

According to one example embodiment, the upstream guide means 53 comprise a retarder 56 arranged in the waveguides between the generating module 12 and the additional filter 52. This retarder makes it possible to delay the transmission of the reference signal relative to the emission signal in order to synchronize this reference signal with the corresponding response signal.

The main filter 51 is able to extract, from the corresponding response signal, elementary signals having different wavelengths.

Thus, in the described example, the main filter 51 is able to extract, from each received response signal, two elementary signals, namely an elementary signal with wavelength $\lambda_A$ and an elementary signal with wavelength $\lambda_B$.

Similarly, the additional filter 52 is able to extract, from each reference signal, two elementary signals, namely an elementary signal with wavelength $\lambda_A$ and an elementary signal with wavelength $\lambda_B$.

The downstream guide means 54 have waveguides connecting the filters 51, 52 to the processing unit 55. These waveguides form, for each filter 51, 52, a separate optical transmission channel for each elementary signal coming from the corresponding filter.

Thus, in the described example, these waveguides form optical transmission channels for each filter 51, 52.

Lastly, the processing unit 55 is able to receive all of the elementary signals transmitted via the downstream guide means 54 to determine the precise composition of the targeted material at several wavelengths. This is done in particular by comparing the spectrums, calculated by Fourier transforms of the interferograms contained in the elementary signals coming from the reference signal and in the reception signal.

The processing unit 55 is for example provided with all necessary hardware or software means configured to carry out said functions.

Figure 3:
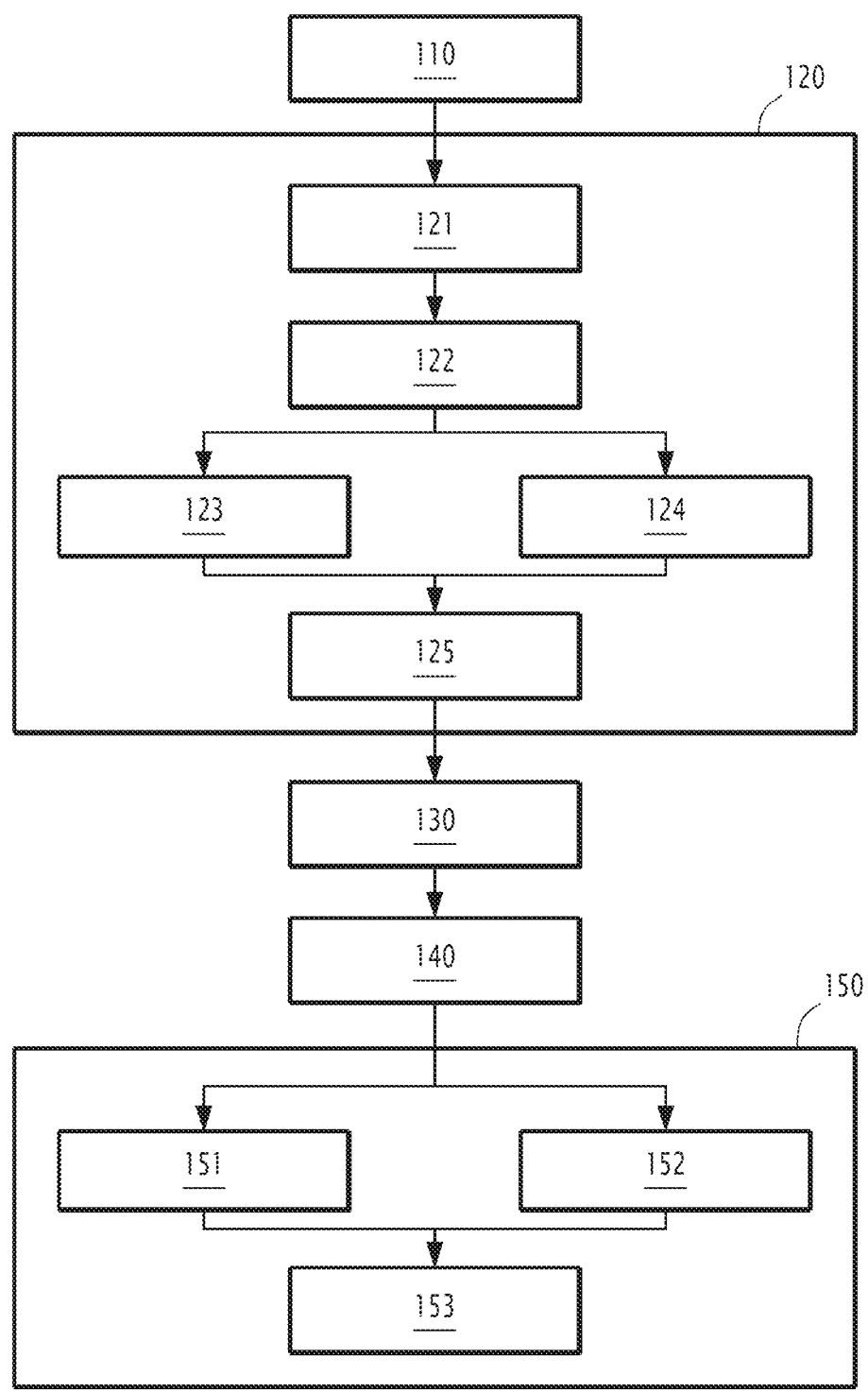
FIG. 3 is a flowchart of a remote spectroscopy method according to the invention, the remote spectroscopy method being carried out by the remote spectroscopy device of FIG. 1.

The remote spectroscopy method implemented by the spectroscopy device 10 will now be explained in reference to FIG. 3, illustrating a flowchart of its steps.

Initially, the targeted material is determined and the emission 14 and receiving 15 modules are configured respectively to send an emission signal towards this material and receive a response signal reflected by this material.

During step 110, the control module 18 commands the generation of an emission signal by the generating module 12.

During the following step 120, the generating module 12 then generates an emission signal intended for the emission module 14 and a reference signal intended for the postprocessing module 16.

This step 120 comprises several sub-steps.

During the initial sub-step 121, the two laser sources 20A, 20B generate two laser signals at wavelengths $\lambda_A$ and $\lambda_B$.

During the following sub-step 122, the upstream mixer 31 mixes the two generated laser signals to form a composite signal. This composite signal is next divided into two equal portions by the upstream separator 32.

During the following sub-step 123, the composite signal passing through the first optical channel 21 is modulated at the first modulation frequency $F_1$. During the sub-step 124 carried out in parallel with the sub-step 123, the composite signal passing through the second optical channel 21 is modulated at the second modulation frequency $F_2$.

During the following sub-step 125, the downstream mixer 48 mixes the modulated signals coming from the optical channels 21, 22 and the downstream separator 49 divides the signal coming from the mixer 48 to form an emission signal and a reference signal.

During step 130 carried out after step 120, the emission module 15 sends the emission signal toward the targeted material.

During the following step 140, the receiving module 15 receives a response signal corresponding to the emission signal reflected by the targeted material.

During the following step 150, the postprocessing module 16 analyzes the response signal and the reference signal to determine the precise composition of the targeted material.

In particular, step 150 comprises several sub-steps.

During the sub-step 151, the main filter 51 receives the response signal received by the receiving module 15 and extracts two elementary signals therefrom at the wavelengths $\lambda_A$ and $\lambda_B$.

During the sub-step 152 carried out in parallel with the sub-step 151, the additional filter 52 receives the delayed reference signal, and extracts two elementary signals therefrom at the wavelengths $\lambda_A$ and $\lambda_B$.

During the following sub-step 153, the main 51 and additional 52 filters send all of the elementary signals to the processing unit, which then analyzes them to determine the precise composition of the targeted material.

Thus, the spectroscopy device and the spectroscopy method implemented by this device make it possible to carry out a more thorough analysis of the targeted material by simultaneously using a spectroscopy at several wavelengths. One can then see that this makes it possible to increase the quality of the spectroscopy for different targeted materials.

Furthermore, it is clear that the invention is not limited to the architecture of the spectroscopy device previously described. In particular, any known architecture further incorporating several laser sources at different wavelengths according to the invention can be used to carry out the invention.

Thus, in the architecture described above, it is possible to eliminate the downstream mixer 48 in order to connect the second optical channel 22 directly to the additional filter 52 of the postprocessing module 16. In this case, only the comb generated by the first optical channel 21 is sent toward the targeted material, while the comb generated by the second optical channel 22 is transmitted directly to the postprocessing module 16 in the reference signal.

Conversely, when the downstream mixer 48 is used, it is possible to completely eliminate the transmission of a reference signal toward the postprocessing module 16. In this case, the beating of the two combs generated at different frequencies in the emission signal is sufficient to determine the precise composition of the targeted material.

Lastly, it is possible to provide a number of laser sources strictly greater than two to cover a greater wavelength domain. Of course, in this case, the main filter and optionally the additional filter must be suitable for extracting as many elementary signals at different wavelengths as there are laser sources.

The invention claimed is:

1. A remote spectroscopy device of the LIDAR type, the remote spectroscopy device comprising:
    A generating module configured to generate an emission signal;
    An emission telescope configured to send the emission signal;
    A receiving telescope configured to receive a response signal corresponding to the emission signal reflected by the targeted material;
    a postprocessing module configured to postprocess the response signal to determine a composition of the targeted material;
    wherein the generating module includes:
    at least two laser sources, each laser source is configured to generate a laser signal at a predetermined wavelength different from the wavelength of the other laser source;
    an upstream mixer configured to mix the laser signals generated by the different laser sources to form a composite signal;
    a first modulator configured to modulate the composite signal to a first modulation frequency to form the emission signal;
    a second modulator configured to modulate the composite signal at a second modulation frequency different from the first modulation frequency; and
    a downstream mixer configured to mix the composite signal modulated by the first modulator and the composite signal modulated by the second modulator to form the emission signal.

2. The device according to claim 1, wherein the postprocessing module includes a main filter configured to extract, from the received response signal, elementary signals corresponding to the different predetermined wavelengths.

3. The device according to claim 1, wherein the generating module further includes a separator configured to separate the composite signal to form the emission signal and a reference signal intended for the postprocessing module.

4. The device according to claim 3, wherein the postprocessing module further includes a complementary filter configured to extract, from the reference signal, elementary signals corresponding to the different predetermined wavelengths.

5. The device according to claim 1, wherein the first modulation frequency is chosen based on physical characteristics of the targeted material.

6. The device according to claim 1, wherein the predetermined wavelengths are chosen based on physical characteristics of the targeted material.

7. A remote spectroscopy method comprising:
    generating an emission signal;
    sending the emission signal toward a targeted material;
    receiving a response signal corresponding to the emission signal reflected by the targeted material;
    analyzing the response signal to determine a composition of the targeted material;
    wherein the generating the emission signal further comprises:
    generating at least two laser signals at different predetermined wavelengths;
    mixing the generated laser signals to form a composite signal;
    modulating the composite signal at a first modulation frequency;
    modulating the composite signal at a second modulation frequency; and
    mixing the composite signals modulated at the first and second modulation frequencies to form the emission signal.

8. The method according to claim 7, wherein the analyzing the response signal further comprises:
    extracting, from the received response signal, elementary signals corresponding to the different predetermined wavelengths.

9. The method according to claim 8, wherein the generating the emission signal further comprises:
    separating the emission signal to form a reference signal; and
    wherein the analyzing the response signal further comprises:
    extracting, from the reference signal, elementary signals corresponding to the different predetermined wavelengths.

* * * * *